US005972650A

United States Patent [19]
Yao

[11] Patent Number: 5,972,650
[45] Date of Patent: Oct. 26, 1999

[54] TETRACYCLINE REPRESSOR REGULATED MAMMALIAN CELL TRANSCRIPTION AND VIRAL REPLICATION SWITCH

[75] Inventor: Feng Yao, Newton Center, Mass.

[73] Assignee: Brigham and Women's Hospital, Boston, Mass.

[21] Appl. No.: 08/883,327

[22] Filed: Jun. 26, 1997

[51] Int. Cl.[6] .......................... C12P 21/00; C12N 15/85; C12N 5/10; C07H 21/04
[52] U.S. Cl. ...................... 435/69.1; 435/320.1; 435/325; 435/366; 536/23.7; 536/24.1; 536/23.5
[58] Field of Search ................................ 435/69.1, 320.1, 435/325, 366, 455; 536/23.1, 23.5, 24.1, 23.7

[56] References Cited

U.S. PATENT DOCUMENTS 5,464,758  11/1995  Gossen et al. .......................... 435/69.1
5,589,362  12/1996  Bujard et al. .......................... 435/69.1

OTHER PUBLICATIONS

Deuschle, et al., "Tetracycline–Reversible Silencing of Eukaryotic Promoters," *Mol. and Cel. Biol.* 15:1907–1914 (1995).
Gossen, et al., "Tight Control of Gene Expression in Mammalian Cells by Tetracycline–Responsive Promoters," *Proc. Natl. Acad. Sci. USA* 89:5547–5551 (1992).
Hennighausen, et al., "Conditional Gene Expression in Secretory Tissues and Skin of Transgenic Mice Using the MMTV–LTR and the Tetracycline Responsive System," *J. Cell. Biochem.* 59:463–472 (1995).
Heuer, et al., "Tet Repressor–tet Operator Contacts Probed by Operator DNA–Modification Interference Studies," *J. Mol. Biol.* 202:407–415 (1988).
Kim, et al., "Tetracycline Repressor–Regulated Gene Repression in Recombinant Human Cytomegalovirus," *J. Virol.* 69:2565–2573 (1995).
Yao, et al., "Physical Interaction Between the Herpes Simplex Virus Type 1 Immediate–Early Regulatory Proteins ICP0 and ICP4," *J. Virol.* 68:8158–8168 (1994).

*Primary Examiner*—David Guzo
*Attorney, Agent, or Firm*—Michael A. Sanzo; Vinson & Elkins L.L.P.

[57] ABSTRACT

The present invention is directed to DNA constructs suitable for gene expression in mammalian cells and which are characterized by the presence of a mammalian promoter under the control of a tet operator/repressor system. The DNA may be used as part of a system for expressing recombinant protein. In addition, the tet operator/repressor system can be used to engineer cis- and trans-destructive viruses which are capable of replicating in the presence of the tet repressor, but not in the absence of the repressor. These viruses can be used either directly in the treatment of patients with corresponding viral diseases, as vehicles for the delivery of nucleic acids that can serve as therapeutic agents and as part of vaccines designed to immunize people or animals against viral diseases.

8 Claims, 10 Drawing Sheets

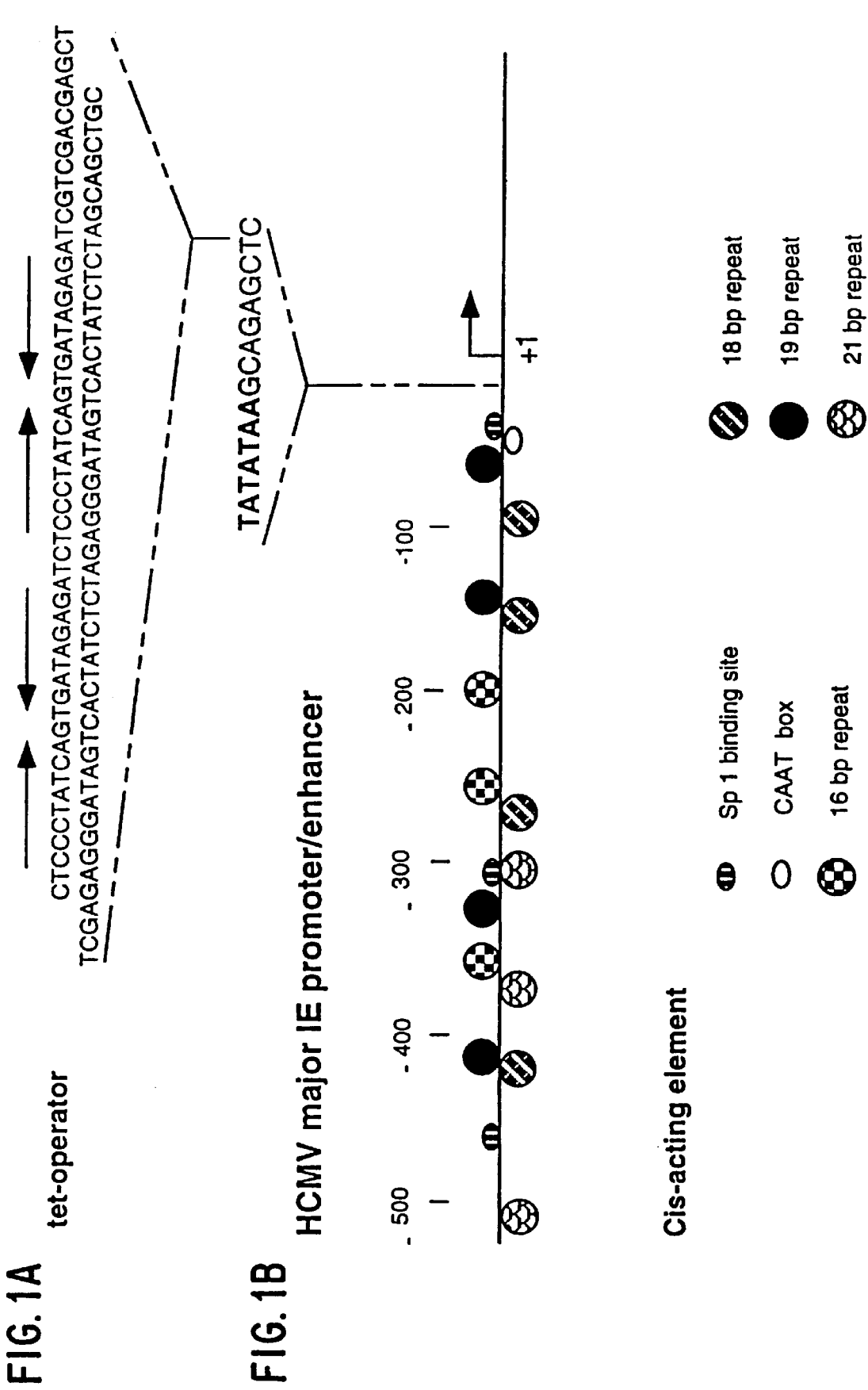

SEQUENCE LISTING

<160> NUMBER OF SEQ ID NOS: 3

<210> SEQ ID NO 1
<211> LENGTH: 54
<212> TYPE: DNA
<213> ORGANISM: Escherichia coli

<400> SEQUENCE: 1
ctccctatca gtgatagaga tctccctatc agtgatagag atcgtcgacg agct          54

```
<210> SEQ ID NO 2
<211> LENGTH: 54
<212> TYPE: DNA
<213> ORGANISM: Escherichia coli

<400> SEQUENCE: 2
tcgagaggga tagtcactat ctctagaggg atagtcacta tctctagcag ctgc        54

<210> SEQ ID NO 3
<211> LENGTH: 16
<212> TYPE: DNA
<213> ORGANISM: Human cytomegalovirus

<400> SEQUENCE: 3
tatataagca gagctc                                                   16
```

TETRACYCLINE REPRESSOR REGULATED MAMMALIAN CELL TRANSCRIPTION AND VIRAL REPLICATION SWITCH

FIELD OF THE INVENTION

The present invention is concerned with compositions and methods that rely upon the tetracycline resistance (tet) operator and repressor to control transcription in mammalian cells. It encompasses methods for recombinantly producing proteins and the vectors and host cells utilized in such methods. In addition, the present invention is directed to viruses which are recombinantly engineered so that their replication is controlled by the tet operator/repressor system. These viruses may serve as vehicles for gene transfer both in vitro and in vivo; as agents for immunization; and as a means for delivering nucleic acid therapeutic agents to cells.

BACKGROUND OF THE INVENTION

The ability to specifically regulate transgene expression has been a central concern in molecular biology for many years. In the case of mammalian cells, the in vitro regulation of recombinant genes has most often been accomplished through the use of inducible promoters that respond to agents such as heavy metal ions (Brinster, et al., *Nature* 296:39–42 (1982); heat shock (Nover, in *Heat Shock Response*, pp. 167–220, CRC, Fla. (1991)); and hormones (Klock, et al., *Nature* 329:734–736 (1987)). Unfortunately, these promoters generally provide only a relatively a low level of expression even in the presence of inducer and most of the inducers that have been used in vitro have unacceptable side effects in vivo.

As an alternative to inducible promoters, attempts have been made to control mammalian gene expression using well-characterized prokaryotic regulatory elements. In most cases, regulatory systems have relied upon strong interactions between prokaryotic operators and repressor proteins as a means for either targeting eukaryotic transcription modulators to specific sites within a host cell genome (see e.g., Labow, et al., *Mol. Cell. Biol.* 10:3343–3356 (1990)) or in attempts to directly inhibit gene expression using the prokaryotic repressor (see e.g., Brown, et al., *Cell* 49:603–612 (1987)).

In the case of prokaryotic elements associated with the tetracycline resistance (tet) operon, systems have been developed in which the tet repressor protein is fused with polypeptides known to modulate transcription in mammalian cells. The fusion protein has then been directed to specific sites by the positioning of the tet operator sequence. For example, the tet repressor has been fused to a transactivator (VP16) and targeted to a tet operator sequence positioned upstream from the promoter of a selected gene (Gussen, et al., *Proc. Nat'l Acad. Sci. USA* 89:5547–5551 (1992); Kim, et al., *J. Virol.* 69:2565–2573 (1995); Hennighausen, et al., *J. Cell. Biochem.* 59:463–472 (1995)). The tet repressor portion of the fusion protein binds to the operator thereby targeting the VP16 activator to the specific site where the induction of transcription is desired. An alternative approach has been to fuse the tet repressor to the KRAB repressor domain and target this protein to an operator placed several hundred base pairs upstream of a gene. Using this system, it has been found that the chimeric protein, but not the tet repressor alone, is capable of producing a 10 to 15-fold suppression of CMV-regulated gene expression (Deuschle, et al., *Mol. Cell. Biol.* 15:1907–1914 (1995)). The main problem with these types of systems is that the portion of fusion proteins corresponding to the mammalian transactivator or repressor tends to interact with cellular transcriptional factors and cause pleiotropic effects.

Ideally, a system for regulating mammalian gene expression should be highly specific for a selected gene and subject to induction by factors suitable for use both in vitro and in vivo. The present invention discloses such a system and describes how it can be used to regulate transgene expression. In addition, the invention describes how this system can be adapted to engineer viruses to serve as vectors, therapeutic agents and vaccines.

SUMMARY OF THE INVENTION

The present invention is directed to a number of different compositions and methods which share the common feature of having gene expression regulated by the tet operator/repressor system.

A. Compositions and Methods for the Production of Recombinant Protein

In its first aspect, the invention is directed to a recombinant DNA molecule which contains a mammalian promoter sequence with a TATA element; at least one tet operator sequence; and a gene sequence operably linked to the promoter and lying downstream from the operator. The exact positioning of the operator sequence (or sequences) relative to the TATA element is critical to the invention. In order to be effective at controlling transcription, the operator must begin at least 6 nucleotides downstream from the last nucleotide in the TATA element and, when a gene encoding a protein is expressed, the operator should be positioned before the translation initiation codon. In general, the operator should not begin more than about 100 nucleotides downstream and, preferably, it should begin within 6 to 24 nucleotides downstream of the TATA element. When positioned in this manner, it has been found that the binding of the repressor protein causes an essentially complete shutdown in transcriptional activity. This is true even for very strong and highly promiscuous promoters such as the human CMV immediate early promoter.

It is expected that the recombinant DNA molecule described above will, most typically, be incorporated into mammalian cells that constitutively express the tet repressor protein. Suitable cells may be developed by transforming a mammalian cell line, e.g., U2OS cells or Vero cells, with a vector containing the tet repressor protein gene operably linked to a promoter active in the cells (e.g., a CMV promoter, HSV-1 promoter or SV40 promoter). Alternatively, the DNA molecule may contain, in addition to the elements already discussed, a second promoter, preferably constitutive, operably linked to the tet repressor gene sequence. The invention encompasses, not only the DNA molecules, but also the host cells transformed with the DNAs and the recombinant proteins made by the cells.

The present invention is also directed to a method for recombinantly producing protein in which mammalian host cells are transformed with a vector containing a mammalian promoter sequence having a TATA element; at least one tet operator sequence positioned at least 6 nucleotides 3' to the TATA element; and a gene lying 3' to the operator and operably linked to the promoter. The gene 3' to the operator may encode an antisense nucleic acid that inhibits the expression of a selected gene, a therapeutically active agent (e.g. a tumor suppressor or a transdominant negative mutant polypeptide of a cellular protein), a protein of interest for experimental purposes or simply a protein whose isolation is desired. In all cases where the gene encodes a protein, the operator sequence will be positioned before the translation initiation codon of the gene. The transformed cells should constitutively express the repressor protein and recombinant gene expression may be induced in the cells by introducing tetracycline. Typically, the tet operator sequence will be located between 6 and 100 nucleotides (preferably between 6 and 24 nucleotides) 3' to the last nucleotide in the TATA element. The preferred promoter is the human CMV immediate-early promoter. It has been found that this system allows for the very tight regulation of gene expression, i.e., expression is essentially completely shut off until the inducer, tetracycline, becomes available.

The method can be used to produce recombinant protein in cultured mammalian cells or in the cells of a transgenic or non-transgenic animal. When a transgenic animal is used for production, it will most typically be a mouse and it is necessary that the cells transformed with the vector described above be embryonic stem cells. The stem cells may be engineered to express the tetracycline repressor by transforming them with the repressor gene operably linked to a promoter prior to transformation with the tet operator and recombinant gene. Alternatively, the repressor gene can be incorporated into the same DNA construct as the tet operator and placed under the control of either the same promoter as the gene encoding the recombinant protein or under the control of a separate promoter. The transformed stem cells are incorporated into a blastocyst to form a chimeric embryo, which is implanted into a pseudopregnant animal. Embryos implanted in this manner are allowed to develop into viable offspring that are screened to identify heterozygous animals expressing the recombinant gene. The heterozygous animals are then bred to produce homozygous animals that make recombinant protein in response to the administration of tetracycline.

The invention encompasses the transgenic animals made using this method and any transgenic animal that has integrated into its genome recombinant DNA containing a mammalian promoter sequence having a TATA element; at least one tet operator sequence positioned at least 6 nucleotides 3' to the TATA element; and a gene lying 3' to the operator and operably linked to the promoter. When the gene encodes a protein, the sequence of the operator will be positioned before the translation initiation codon of the gene. Typically, the tet operator sequence will be located between 6 and 100 nucleotides (preferably between 6 and 24 nucleotides) 3' to the last nucleotide in the TATA element. The preferred promoter is the human CMV immediate-early promoter. In addition to the transgenic animals, the invention encompasses the recombinant proteins made by these animals.

B. Engineered Viruses and Their Uses

One particularly important use of the tet operator/repressor expression system is in the making of viruses in which replication can be controlled. The essential characteristic of these viruses is that they contain within their genome at least three related elements: a recombinant promoter having a TATA element; at least one tet operator sequence positioned at least 6 nucleotides 3' to the TATA element; and a gene operably linked to the promoter, which lies downstream from the operator and which inhibits viral replication when expressed. Typically, the tet operator sequence will be located between 6 and 100 nucleotides (preferably between 6 and 24 nucleotides) 3' to the last nucleotide in the TATA element. The gene lying downstream of the operator may act either by encoding a protein that inhibits viral replication or by forming a transcription product that inhibits viral replication through an antisense mechanism. When the gene encodes a protein, the tet operator sequence will be positioned upstream from the translation initiation codon. The engineered virus can be made and grown in cultured cells that constitutively express the tet repressor protein. Under these conditions, the gene that inhibits viral replication will be shut off, allowing large amounts of virus to be produced. Virus may then be collected, purified, and introduced into mammalian cells either in vitro or in vivo. Since mammalian cells do not normally make the tet repressor protein, the operator sequence will be unoccupied. As a result, the gene lying 3' to the tet operator is expressed and viral replication is prevented.

Viruses engineered in the manner discussed above have a wide range of possible applications. First, the viruses can be used as a vehicle for delivering DNA, (e.g., a gene) to mammalian cells. Under these circumstances, a second recombinant promoter will typically be incorporated into the viral genome and operably linked to the gene whose expression is desired. This second promoter may or may not, be followed by one or more tet operators lying between 6 and 100 (preferably between 6 and 24) nucleotides downstream from a TATA element in the second recombinant promoter. After having delivered the DNA to the host cell, production of new virus is inhibited due to the absence of the tet repressor protein. The gene attached to the second promoter may encode an antisense nucleic acid that inhibits the expression of a selected gene within cells; a therapeutically active protein (e.g., a tumor suppressor or a transdominant negative mutant polypeptide of a cellular protein); or simply a protein that will be isolated or that is of interest for experimental reasons. The invention encompasses the method of transforming host cells by transfecting them with the virus, the transformed host cells themselves and the recombinant proteins made by the host cells.

The viruses discussed above may also be used to immunize subjects. The great advantage of vaccines containing the engineered viruses that, because the viruses will not replicate after they are injected into subjects, the risk of active viral infection due to immunization is greatly reduced. To further ensure that virus replication will not occur, additional mutations may be introduced into the viruses, e.g. a deletion mutation may be introduced into one or more essential viral genes. In general, viruses containing such additional mutations will be preferred.

The engineered viruses also have utility in the direct treatment of patients for viral infections. The first step in this method involves transforming a second virus (i.e., a virus other than the one that has infected the patient although possibly of the same strain) by incorporating into its genome: DNA comprising a mammalian promoter with a TATA element; at least one tet operator sequence positioned at least 6 nucleotides 3' to the TATA element (typically between 6 and 100 nucleotides 3' to the TATA element); and a gene positioned 3' to the operator and operably linked to the promoter. This gene should be chosen so that, when expressed, it is capable of blocking the replication of both the second virus and the virus which has infected the patient. In cases where the gene encodes a protein, the sequence of the tet operator will be positioned before the translation initiation codon of the gene. The transformed second virus is grown in host cells expressing the tet repressor protein, thereby allowing large amounts of viral progeny to be produced. Virus is collected, purified and then administered to the patient. In preferred embodiments, the tet operator is located between 6 and 24 nucleotides downstream from the last nucleotide in the TATA box and the promoter used is the human CMV immediate-early promoter.

Finally, the present invention is directed to a method for delivering a nucleic acid therapeutic agent to cells. The nucleic acid therapeutic agent may comprise either an antisense fragment that inhibits the expression of a cellular protein, or a gene that encodes a protein with a therapeutic action. The virus is engineered to contain within its genome: i) a recombinant mammalian promoter with a TATA element; at least one tet operator sequence positioned at least 6 nucleotides 3' to the TATA element and 5' to a translation initiation codon; and iii) a gene positioned 3' to the operator and operably linked to the promoter. When this gene is expressed, viral replication is inhibited. Typically, the tet operator sequence will be located between 6 and 100 nucleotides (preferably between 6 and 24 nucleotides) 3' to the last nucleotide in the TATA element. The preferred promoter is the immediate-early promoter of human CMV. In addition, the virus must contain within its genome the nucleic acid encoding the therapeutic agent operably linked to a second promoter. This second promoter may, or may not, be followed by one or more tet operators lying, typically, between 6 and 100 (preferably between 6 and 24) nucleotides downstream from a TATA element in the second promoter.

After the preparation of the viral vector for delivering therapeutic agent, the next step in the method is to grow a large amount of the virus in a host cell that expresses the tet repressor protein. The virus grown in this manner is collected, purified and then administered to the patient. Since the patient would not normally have cells synthesizing tet repressor, replication of virus will be blocked but transcription of the nucleic acid therapeutic agent will proceed.

BRIEF DESCRIPTION OF THE FIGURES

FIG. 1. Parts A–B Diagram of the hCMV major immediate-early enhancer-promoter and strategy for creating a tetR-responsive transcription switch. Panel A shows a DNA sequence containing two tandem tet operators used for generating the tet operator-bearing hCMV major immediate-early enhancer-promoter. The topmost sequence in panel A is designated SEQ ID NO:1. Its complementary sequence is SEQ ID NO:2. The lowermost sequence in the panel is designated SEQ ID NO:3. Panel B shows DNA sequences surrounding the TATA element and cis-acting sequences known to interact with cellular transcription factors. A Sac I restriction site used for insertion of tet operator is underlined.

DEFINITIONS

Figure 2A:
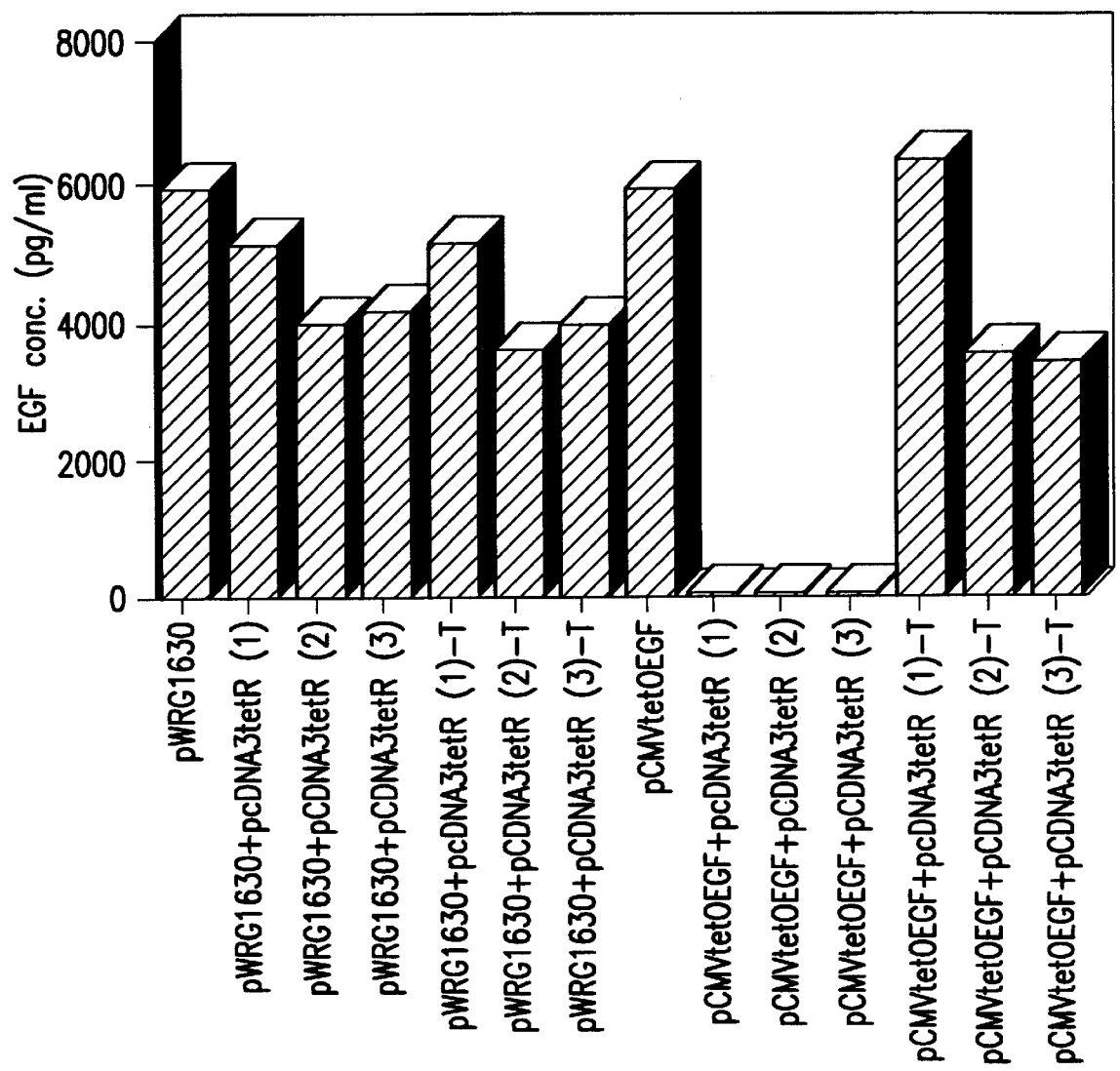
FIG. 2. Parts A–C Insertion of tet operator sequences immediately downstream of the TATA element converts the hCMV major immediate-early enhancer-promoter to a tetR-sensitive transcription switch. Vero cells were seeded at $3\times10^5$ cells per 60 mm dish and, at 24 hours after seeding, cells were transfected with 0.5 $\mu$g of pWRG1630 or pCMVtetOEGF alone or in the presence of 1 $\mu$g, 2 $\mu$g and 3 $\mu$g of the tet repressor-expressing plasmid, pcDNA3-tetR, either in the absence or presence of tetracycline at 1 $\mu$g/ml. pUC19 vector plasmid was used to balance the pCDNA3-tetR and 3.5 $\mu$g of plasmid DNA was used in the transfection assay. Extracellular medium was collected from transfected cells every 20–24 hours and fresh growth medium was added either with or without 1 $\mu$g/ml of tetracycline. hEGF in extracellular medium collected from 0 to 20 hours (panel A), 20 to 44 hours (panel B), and 44 to 68 hours (panel C) was determined by ELISA with the use of anti-hEGF specific monoclonal and polyclonal antibodies.

The description that follows uses a number of terms that refer to recombinant DNA technology. In order to provide a clear and consistent understanding of the specification and claims, including the scope be given such terms, the following definitions are provided.

Viral vector: As used herein, "viral vector" and equivalent terms refer to viruses that are utilized for transferring selected DNA or RNA sequences into a host cell. The vectors maybe utilized for the purpose of transferring DNA into cells either in vitro or in vivo. Viruses that have been commonly used for the latter purpose include the retroviruses, adenoviruses, parvoviruses and herpes viruses.

Expression vector: This and comparable terms refer to a vector which is capable of inducing the expression of DNA that has been cloned into it after transformation into a host cell. The cloned DNA is usually placed under the control of (i.e., operably linked to) certain regulatory sequences such a promoters or enhancers. Promoters sequences maybe constitutive, inducible or repressible.

Substantially pure or purified: As used herein, "substantially pure" or "purified" means that the desired product is essentially free from contaminating cellular components. Containments may include, but are not limited to, proteins, carbohydrates and lipids. One method for determining the purity of a protein or nucleic acid is by electrophoresis in a matrix such as polyacrylamide or agarose. Purity is evidence by the appearance of a single band after staining.

Host: Any prokaryotic or eukaryotic cell that is the recipient of a vector is the host for that vector. The term encompasses prokaryotic or eukaryotic cells that have been engineered to incorporated a gene in their genome. Cells that can serve as hosts are well known in the art as are techniques for cellular transformation (see e.g., Sambrook, et al., *Molecular Cloning: A Laboratory Manual,* 2nd ed., Cold Spring Harbor (1989)).

Promotor: A DNA sequence that initiates the transcription of a gene. Promoters are typically found 5' to the gene and located proximal to the start codon. If a promotor is of the inducible type, then the rate of transcription increases in response to an inducing agent.

Expression: Expression is the process by which a polypeptide is produced from DNA. The process involves the transcription of the gene into mRNA and the translation of this mRNA into a polypeptide. Depending on the context in which used, "expression" may refer to the production of RNA, protein or both.

Recombinant: As used herein, the term "recombinant" refers to nucleic acid that is formed by experimentally recombining nucleic acid sequences and sequence elements. A recombinant host would be any host receiving a recombinant nucleic acid and the term "recombinant protein" refers to protein produced by such a host.

Operably linked: The term "operably linked" refers to genetic elements that are joined in such a manner that enables them to carry out their normal functions. For example, a gene is operably linked to a promotor when its transcription is under the control of the promotor and such transcription produces the protein normally encoded by the gene.

Nucleic acid therapeutic agent: This term refers to any nucleic acid sequence which directly, or indirectly, serves as a therapeutic agent. Typically, such agents will fall into two categories. The first category encompasses antisense nucleic acids that are designed to anneal to complementary sequences within the host cell, thereby inhibiting expression. Alternatively, the term may refer to nucleic acids that encode a therapeutic protein.

Gene: As used herein, "gene" refers to the nucleic acid sequence that undergoes transcription as the result of promoter activity. A gene may code for a particular protein or, alternatively, code for an RNA sequence that is of interest in itself, e.g. because it acts as an antisense inhibitor.

Mammalian promoter: The term "mammalian promoter" refers to promoters that are active in mammalian cells. Similarly, "prokaryotic promoter" refers to promoters active in prokaryotic cells.

Essential viral gene: The term "essential viral gene" is defined as a gene that is necessary for viral replication.

Essential cellular gene: This refers to a gene that is necessary for cellular survival

DETAILED DESCRIPTION OF THE INVENTION

The present invention is based upon the concept that is it possible to regulate mammalian gene expression using the tet operator and repressor protein. Provided that the operator is positioned at least 6 nucleotides downstream from the last nucleotide of the TATA element of the promoter controlling expression, regulation can be accomplished without the need to fuse the repressor protein to other mammalian transcription modulators.

Although not critical, a knowledge of the basic functioning of the tetracycline resistance (tet) operon in bacteria may help in understanding the way in which the invention works. In the tet operon, a tetracycline resistance gene (tetA) and gene encoding the tet repressor protein (tetR) are both under the control of the same promotor and operator elements. In the absence of tetracycline, the tet repressor protein binds to the operator DNA sequence, thereby sterically preventing the adjacent promoter from interacting with RNA polymerase. Thus, transcription of both tetA and tetR are blocked. When the level of tetracycline within the bacterium increases, the tetracycline binds to the repressor protein causing it to detach from the operator sequence. As a result, the polymerase is able to bind to the promotor sequence and both the tetA and tetR genes are transcribed.

The strong interaction between the tet repressor protein and the tet operator has provided a mechanism for targeting eukaryotic regulatory proteins to specific sites within the genome of a cell. As discussed above, previous systems have been described in which the tet operator is positioned upstream from a mammalian gene to serve as a target for fusion proteins comprised of the tet repressor and a mammalian transcription activator or repressor. The tet repressor portion of the fusion protein binds to the operator sequence, thereby positioning it upstream from the gene to be expressed. The remaining portion of the fusion protein then serves to modulate gene expression by interacting with cellular transcription factors.

The main problem with these types of systems is that pleiotropic effects are caused by the interaction of the mammalian transcription modulator with transcriptional factors at sites distinct from the operator. Previous attempts to modulate gene expression using the tet repressor protein alone, (i.e., other than as a fusion protein) have been unsuccessful (see e.g., Kim, et al., *J. Virol.* 69:2565–2573 (1995); Deuschle, et al., *Mol. Cell. Biol.* 15:1907–1914 (1995)). It has now been discovered that successful modulation of gene expression using tetR alone can be accomplished by inserting one or more tet operators approximately 10 base pairs, a full DNA helix turn, downstream of the tet operator. Using this approach, it has been possible to tightly regulate transcription controlled by the hCMV major immediate-early enhancer-promotor, one of the most potent and promiscuous eukaryotic elements. This can be done both in vitro and in vivo.

I. The Tet Operator as a Transcriptional Switch

In its first aspect, the present invention is directed to recombinant DNA molecules containing a mammalian promoter sequence with a TATA element. A tetracycline operator sequence is positioned at least 6 nucleotides 3' to the TATA element and is followed by a DNA sequence whose transcription is controlled by the promoter. Procedures for either synthesizing or purifying promoters, operators and other DNA sequences are well known in the art and standard techniques in molecular biology can be employed for constructing DNA molecules with appropriately arranged elements (see e.g., Sambrook et al., *Molecular Cloning: A Laboratory Manual*, 2nd ed., Cold Spring Harbor Press (1989)). Examples of preferred methods are provided in the "Examples" section along with the complete sequence of the tet operator.

Any type of promoter active in mammalian cells can be used in the invention including those that are inducible, repressible or constitutive. Preferred mammalian promoters include that of the mouse metallothionein I gene (Hamer, et al. *J. Mol. Appl. Gen.* 1:273–288 (1982)); the immediate-early and TK promoter of herpes virus (Yao et al., *J. Virol.* 69:6249–6258 (1995); McKnight, *Cell* 31:355–365 (1982)); the SV 40 early promotor (Benoist, et al., *Nature* 290:304–310 (1981)); and, especially, the human CMV immediate-early promoter (Boshart, et al. *Cell* 41;521–530 (1985)). Full length or minimal promoters may be used and other regulatory elements, (see e.g. FIG. 1) may be included. As discussed in the "Examples" section, the full human CMV major immediate-early enhancer-promotor has been successfully used in the invention and it will be understood that, unless otherwise specified, reference to the "human CMV immediate-early promoter" includes both the promoter per se, as well as the promoter in combination with any or all of the other transcriptional regulatory elements shown in FIG. 1.

The promotor is separated from the sequence undergoing transcription by one or more tet operator sequences that begin at least 6 nucleotides downstream from the TATA element. Typically, the operator will begin at a position between 6 and 100 nucleotides (and preferably between 6 and 24 nucleotides) downstream from the TATA element. The arrangement of these elements must not substantially interfere with the ability of the promoter to direct the transcription of the downstream sequence or the translation of the gene product.

Typically, the DNA molecule described above will be incorporated into a vector (e.g. a plasmid or virus) which contains other transcription or translational elements. If desired, large amounts of vector DNA can be generated, (e.g., but transferring the vector into bacteria that make the repressor protein). Preferably, the vector is then transferred into a mammalian host cell which has been engineered to express the tet repressor. One way to engineer mammalian cells to express the tet repressor is to operably link the repressor gene sequence to a second promoter, incorporate this into the vector containing the tet operator and then transfer the DNA into the cells. Alternatively, cells may be transformed with an expression vector containing the tet repressor sequence prior to the transfer of the construct containing the tet operator. An example of a plasmid that has been used to produce cells expressing the tet repressor is pcDNA3-tetR (see "Examples" section).

Any method for introducing expression vectors into cells maybe used with the present invention including calcium phosphate precipitation, microinjection, electroporation, liposomal transfer, viral transfer or particle mediated gene transfer. When transfers are done to host cells in vivo, the preferred method of transformation is by means of a viral vector. Cells that have incorporated constructs can be identified using hybridization techniques well known in the art or by using the polymerase chain reaction (PCR) to amplify specific recombinant sequences. If the recombinant DNA transferred into the cells produces a protein that can be detected, e.g., by means of an immunological or enzymatic assay, then the presence of recombinant protein can be confirmed by introducing tetracycline into cells and then performing the assays either on the medium surrounding the cells or on cellular lysates.

In the absence of tetracycline, host cells transformed with the constructs should not express substantial amounts of recombinant DNA. Expression of recombinant DNA sequences incorporated into hosts cells is induced using either tetracycline per se or a tetracycline analogue. The latter is defined as any compound which is related to tetracycline in the sense that it maintains the ability to bind with specificity to the tet repressor. The dissociation constants of such analogues should be at least $1 \times 10^{-6}$ M and preferably greater than $1 \times 10^{-9}$ M. Examples of analogues that can be used include, but are not limited to, those discussed by Hlavka, et al. ("The Tetracyclines," in *Handbook of Experimental Pharmacology* 78, Blackwood, et al. (eds.), New York (1985)) and Mitschef ("The Chemistry of Tetracycline Antibiotics," *Medicinal Res.* 9, New York (1978)). Similarly, minor modifications in the sequence of the repressor or the operator will not affect the invention provided that such modifications do not substantially reduce either the affinity or specificity of the repressor/operator interaction.

II. Method for Recombinantly Producing Protein in Vitro and in Vivo

The vectors and DNA constructs discussed above can be used as part of a method for recombinantly producing protein either in vitro or in vivo. In vitro, mammalian host cells are preferred for the production of protein and include U2OS cells, Vero cells, NIH-3T3 cells, CHO cells, Hela cells, LM(tk-) cells, etc. Vectors suitable for use in each of these various cell types are well known in the art (see e.g., Sambrook, et al., supra).

The DNA constructs may also be used to produce recombinant proteins in vivo using both transgenic and non-transgenic animals. Although production in any type of transgenic animal is compatible with the invention, it is expected that mice will be used in most cases. Typically, mouse embryonic stem (ES) cells will be transformed with the DNA constructs and then incorporated into a developing mouse embryo. Any ES cell line which has the ability to integrate into and become part of the germ line of the developing embryo may be used, e.g., the murine cell line D3 (ATCC, 12301 Parklawn Drive, Rockville, Md., catalog no. CR 1934). The cells are cultured and prepared for DNA insertion using methods well-known in the art (See, e.g., Robertson, in *Teratocarcinomas and Embryonic Stem Cells;*

*Practical Approach*, Robertson, ed., I.R.L. Press Washington, D.C. (1987); Bradley, et al., *Current Topics in Devel. Biol* 20; 357–371 (1986); and Hogan, et al., *Manipulating the Mouse Embryo; A Laboratory Manual*, Cold Spring Harbor Laboratory Press, Cold Spring Harbor, M.Y. (1986)). Stem cells will need to be engineered to express the tet repressor protein, and, as discussed above, this can be done either by incorporating the repressor gene into the same construct containing the tet operator or by separately transforming cells with a repressor gene-containing construct.

DNA can be incorporated into cells using any method known in the art, but most typically, this transfer will be accomplished using electroporation. If the DNA construct has been inserted into a plasmid-type vector, it is preferred that the DNA be linearized prior to transfection. Linearization can be accomplished by digesting the DNA vector with a suitable restriction endonuclease selected to cut outside of the DNA sequence to be expressed. The screening of transfected stem cells can be carried out using any of a variety of methods. For example, Southern hybridizations may be carried out using labeled probes that are specific to a sequence located within the DNA transferred into cells. Alternatively, PCR amplification can be used for selected sequences.

After embryonic stem cells have been transformed and selected, the next step is to incorporate the cells into an embryo. The preferred method for accomplishing this is by microinjection of the stem cells into an embryo at the blastocyst stage of development. In mice, blastocysts at about 3.5 days of development may be obtained by perfusing the uterus of pregnant animals. Appropriate methods for carrying this out are well known in the art (see Bradley, in *Teratocarcinomas and Embryonic Stem Cells; A Practical Approach*, (1987)). Preferred blastocysts are male and have genes s for a phenotypic marker (e.g. coat color) that is different from the phenotypic marker encoded by the stem cell genes. In this way, offspring can be easily screened.

The next step in the process of producing transgenic animals involves implanting the chimeric embryo into the uterus of a pseudopregnant animal. Such animals are typically prepared by mating females with vasectomized males of the same species. The pseudopregnant stage of the female is important for successful implantation and will vary from species to species. For mice, females about two to three days pseudopregnant should typically be used.

After chimeric embryos have been implanted into pseudopregnant animals, they are allowed to develop to term and offspring are then screened. In cases where a phenotype selection strategy has been employed, initial screening may be accomplished by simple inspection of animals for mosaic coat color or for some other readily apparent phenotypic marker. In addition, or as an alternative, chromosomal DNA may be obtained from the tissue of offspring, e.g., from the tail tissue of mice, and screened for the presence of recombinant DNA using Southern blots and/or PCR amplification. Homozygous transgenic animals may then be produced by interbreeding heterozygotes and then used to provide a continual supply of animals that are capable of expressing recombinant DNA. Expression can be controlled by maintaining the animals in the absence of tetracycline until recombinant synthesis is desired. Under these conditions, the tet repressor protein will bind to the operator sequence thereby inhibiting the activity of the recombinant promoter. Tetracycline, or a tetracycline analog, once administered to animals will readily cross cell membranes and then cause the tet repressor protein to dissociate from the operator sequence. Thus, the recombinant gene downstream from the recombinant promoter will start being transcribed.

Animals made in this manner, may be used for research purposes, e.g., to study the effects of various drugs or, alternatively, they may be used for the purpose of producing recombinant protein. In the latter case, it is preferred that the recombinant genes expressed in the cells be linked to a signal sequence that causes protein to be secreted into the blood of the animals. This may then be collected to serve as a source for the purification of recombinant protein.

III. Recombinantly Engineered Virus

A. The Making of Recombinant Virus, Vaccines and Anti-viral Treatment

The tet operator/repressor regulatory system described above can be used to engineer viruses in which the production of progeny is tightly regulated. This can be done by incorporating into the viral genome a construct containing a promoter (preferably the human CMV immediate-early promoter), the tet operator sequence at a position at least 6 nucleotides 3' to the TATA element and a gene 3' to the operator and operably linked to the promoter. This gene inhibits viral replication when expressed and may take the form of an antisense sequence that binds to RNA encoding a protein necessary for viral replication or, alternatively, the gene may encode a protein that inhibits replication. In the latter case, the tet operator sequence will be positioned before the translation initiation codon of the gene. An example of a protein that will inhibit viral replication is the transdominant negative form of the UL9 protein of HSV-1 which binds to the HSV-1 origin of replication and, when over-expressed, blocks new viruses from being formed. Similar proteins have been found to exist in many other viruses as well.

Viruses as described above can be generated in cells that constitutively produce the tet repressor protein. Under these circumstances, the repressor will bind to the tet operator sequence and inhibit the expression of the gene downstream. Thus, viral inhibitory DNA sequences can be incorporated into the viral genome and large amounts of virus can be produced. For example, the repressor might block the synthesis of the mutant form of the UL9 protein, thereby allowing the production of HSV-1. If desired, tetracycline or a tetracycline analog may be introduced into cells. The tetracycline will bind to the repressor protein and thereby cause it to dissociate from the operator sequence. Transcription of nucleic acid from the recombinant promoter would then proceed and viral replication would be inhibited.

It should be noted that the system described above can be used both in vitro and in vivo. For example, large amount of virus can be grown by infecting cultured cells that make the tet repressor protein. The viruses can then be collected, purified and administered to a subject. Once administered, the virus delivers its DNA to the cells within the subject but, because the tet repressor protein is not present, transcription of recombinant DNA within the viral genome proceeds and viral replication is inhibited. These characteristics, in themselves, make the engineered virus particularly attractive for use in immunization procedures and in the treatment of viral diseases.

B. The Use of Engineered Virus in Immunization Procedures

Most immunization procedures are carried out by exposing a subject to a particular disease-causing agent which has been modified so that it provokes an immunological response without actually causing the disease. For example, vaccines containing either dead or attenuated virus may be given to an individual to immunize them against polio.

Viruses engineered using the tet operator/repressor system can be grown in large numbers in cultured cells making the tet repressor and then administered to patients as part of a vaccine. The patients thus treated would be exposed to the proteins normally present on the virus and will therefore mount an immunological response. However, because mammalian cells do not normally make the tet repressor, the virus will not be able to replicate and full-fledged exposure to the disease will be prevented.

In order to further ensure that the virus is not made, additional mutations can be introduced into the recombinant virus. For example, a deletion mutation may be introduced into an essential viral gene. The latter virus could be made and grown in cells expressing both tetR and the wild type form of the essential viral gene.

This approach to immunization could be used for virtually all infectious viruses that have been isolated and could be applied both to the immunization of people as well as animals.

C. The Use of Engineered Virus in the Treatment of Viral Diseases

Viruses engineered using the tet operator/repressor system of the present invention can be used directly in the treatment of viral infections. For example, an HSV-1 virus could be engineered in the manner described above to contain within its genome a construct made up of a strong mammalian promoter, the tet operator sequence and the gene encoding the transdominant negative mutant form of UL9. The engineered HSV-1 could be grown in large numbers in cultured cells expressing the tet repressor and then administered to patients suffering from an HSV-1 infection. The engineered virus would enter into the patient's cells and express the transdominant negative mutant UL9 protein. This would serve to inhibit not only the replication of the engineered HSV-1 but also the HSV-1 that had originally infected the patient. In effect, the engineered virus is serving as a vehicle for delivering antiviral agents in vivo. Because the engineered virus shares the same cellular specificity as the infecting virus, it is ideally suited for therapy.

The animal and human viruses for which engineered virus could serve as either a vaccine or therapeutic agent include, without limitation, arboviruses; avian leukosis virus; CELO virus; Chagres virus; rhinoviruses; Coxsackie virus; hemorrhagic viruses; equine encephalomyelitis virus; hepatitis viruses; herpes viruses; infectious porcine encephalomyelitis virus; influenza viruses; Newcastle disease virus; papilloma virus; parainfluenza viruses; poliomyelitis virus; respiratory syncytial virus; Rous sarcoma virus; St. Louis encephalitis virus; dengue virus; Sendai virus; and rabies virus.

D. Engineered Viruses as Vectors for the Delivery of Nucleic Acid Therapeutics

With minor modifications, the engineered viruses discussed above can be used for delivering any type of nucleic acid therapeutic agent to cells. These agents may take the form of either antisense nucleic acids that bind to complementary sequences to inhibit their expression as proteins, or as genes encoding proteins with a therapeutic action.

The nucleic acid sequence that will be used as a therapeutic agent must be operably linked to a promoter which is active in the cells in which therapy is needed. This may either be the same promoter regulating the recombinant gene controlling viral replication or, alternatively, a second distinct promoter within the viral genome. The basic procedure to be followed in treating patients is essentially the same as that discussed above in connection with the use of engineered viruses for treating viral infections. Specifically, the virus engineered to contain nucleic acid therapeutic agent will be grown in cells that produce the tet repressor protein. Viruses made in this manner are collected, purified and administered to the subject in need of treatment. The engineered viruses then infect the subject's cells and, once inside, begin expressing both the nucleic acid inhibiting viral replication and the nucleic acid serving as a therapeutic agent. Although this system is ideally suited to gene therapy, it can also be utilized as a mechanism for delivering nucleic acids to cells in vitro, or as a means for attempting to engineer cells in vivo. For example, DNA constructs designed for homologous recombination to either replace defective counterparts or prevent abnormal gene expression may be delivered in this manner.

As discussed above, additional mutations may be introduced into an essential viral gene in order to ensure that virus is not replicated.

EXAMPLES

Example 1

Conversion of Human CMV Major Immediate-early Enhancer-promoter to a Regulatory Switch Using the tet Repressor A. Materials and Methods Reporter and tet Expression Plasmids: Plasmid pWRG1630 is a human EGF expression plasmid in which a sequence coding for mature hEGF is controlled by the hCMV major immediate-early enhancer-promoter. There are two Sac I sites in pWRG1630 and one of these Sac I sites is located three bases downstream of the TATA element of the hCMV major immediate-early promoter. To construct pCMVtetOEGF, the oligonucleotide:

```
5'-CTCCCTATCAGTGATAGAGATCTC-
   CCTATCAGTGATAGAGAT CGTCGACG
   AGCT-3'                          SEQ ID NO:1
``` and its complementary sequence were annealed and purified by 15% polyacrylamide gel electrophoresis as previously described (Yao, et al., *J. Virol.* 68:8158–8168 (1994)). The tetracycline (tet) operator sequence is shown in bold face (Heuer, et al. *J. Mol. Biol.* 202:407–415 (1988)) and the Sal I restriction enzyme site used for cloning analysis is underlined. The purified double stranded tet operator-containing fragment was then inserted at the Sac I site of the hCMV immediate-early promoter in plasmid pWRG1630 by partial digestion of pWRG1630 with Sac I. The insertion of a tetO sequence in pWRG1630 created a unique Sal I site and insertion of tetO in the hCMV immediate-early promoter created an Eco RI-Bam HI hCMV promoter-containing fragment of 701 base pairs. FIG. 1 shows a schematic diagram of the tetO-containing hCMV immediate-early promoter in plasmid pCMVtetOEGF used in the study.

pCMVGL2 and pCMVtetOGL2 are plasmids derived from a pGL2-basic vector (Promega, Madison, Wis.) in which the cDNA-encoding firefly luciferase is under the control of the wild-type hCMV promoter or the tetO-bearing hCMV promoter. To generate these two plasmids, the Eco RI-Bam HI hCMV promoter-containing fragment from pWRG1630 or the hCMV-tetO promoter-containing fragment from pCMVtetOEGF was inserted into the Sma I and Bgl II site of the pGL-basic vector.

The tetracycline repressor expressing plasmid, pcDNA3-tetR, was constructed by first inserting the Bgl I-Sal I-tetR containing fragment of pSG5tetR into the Xba I and Sal I site in pGEM3Z to generate pGEM3Z-tetR. The Sal I and Kpn I-tetR fragment of pGEM3Z-tetR was then cloned into the EcoR V-Kpn I site in the pcDNA3 vector.

Cell Culture and Transfection

African green monkey kidney (Vero) cells were grown and maintained in Dulbecco's modified Eagle's medium (DMEM) supplemented with 10% fetal bovine serum. Cells were seeded at 2 to $3 \times 10^5$ cells per 60 mm dish. At 20 to 24 hours post-seeding, cells were transfected with either 0.5 μg of pWRG1630 or 0.5 μg of pCMVtetOEGF in the presence of 2 μg of pUC19 vector DNA or 2 μg of pcDNA3-tetR by lipofectin-mediated transfection. The transfection was carried out in serum and antibiotic free DMEM for 16–20 hours followed by removal of the transfection medium and addition of 5 ml of normal growth medium in the presence or absence of tetracycline. The preparation of lipofectin-DNA complexes was carried out according to the procedure of the manufacturer (GIBCOBRL, Life Technologies) at 10 μl of lipofectin per 2.5 μg of plasmid DNA.

For luciferase assays, Vero cells were seeded and transfected in a manner similar to that described above, with the exception of using 0.5 μg of pCMVtetOGL2 in the presence of 2 μg of pUC19 vector DNA, or 2 μg of pcDNA3-tetR. At 20 hours after transfection, the lipofectin-plasmid DNA containing medium was removed and cells were re-fed with normal growth medium in the presence or absence of 1 μg/ml of tetracycline. Cells were harvested at 70–72 hours post-transfection and cell extracts were prepared according to the protocol described by the manufactured (Promega).

Particle-Mediated Gene Transfer:

Pigs used for in vivo gene transfer were domestic female Yorkshire pigs, 3 to 4 months old and weighing 40–45 kg. Partial thickness wounds (15×15×1.2 mm) were made on porcine dorsal skin with a dermatome using Halothane (1–1.5%) anesthesia in a 3:5 mixture of oxygen/nitrous oxide.

Preparation of cartridges with coated DNA-gold beads for Accell (Agracetus/Geniva, Inc.) particle-mediated gene transfer and the utilization of the Accell helium gene gun were according to the protocol provided by Geniva, Inc. (8520 University Green, Middleton, Wis. 53562). Each partial thickness wound was provided with 0.2 μg of hEGF expressing plasmid and 0.8 μg of pcDN4A3 or 0.2 μg hEGF expressing plasmid and 0.8 μg of pcDNA3-tetR. The driving pressure used was 800 pounds per square inch (psi). Following DNA transfer, the transfected wounds were enclosed in sealed vinyl adhesive chambers containing 1.2 ml of isotonic saline in the presence of 100 units/ml penicillin and 100 μg/rnl streptomycin. Wound fluid was withdrawn from the chambers at 22 hours post-gene transfer and the transfected sites were enclosed in new chambers. Following the collection of wound fluid and application of new chambers at 46 hours after gene transfer, pigs were given 500 mg of tetracycline by intravenous injection. At 24 hours after the administration of tetracycline, wound fluid was collected and stored at −70 degrees C. Levels of EGF in wound fluid was determined by ELISA with anti-HEGF specific antibody.

ELISA:

Expression of hEGF in extracellular medium and wound fluid was determined on microtiter plates (96 wells) with the use of anti-hEGF specific monoclonal antibody (MAB236, R&D systems) as the primary coating antibody at 75 ng per well and anti-hEGF specific polyclonal antibody (sc275, Santa Cruz) as secondary antibody at 100 ng per well. The HRP-conjugated goat anti-rabbit polyclonal antibody (sc-2004, Santa Cruz) was used as tertiary antibody at 3.33 ng per well. The peroxidase assay was performed according to the procedures of the TMB peroxidase EIA substrate kit (BIO-RAD) and analyzed on a Bmax Kinetic Microplate Reader (Molecular Devices Corporation, Sunnyvale, Calif.). The concentration of hEGF in samples was fit to a SOFTmax 4-parameter standard curve generated with the use of recombinant hEGF (234-EG, R&D systems) in a two-fold dilution ranging from a concentration of a 2 pg to 200 pg/ml in a volume of 200 μl per well.

B. Results.

In Vitro Regulation of the hCMV Major Immediate-Early Enhancer-Promoter by the Tetracycline Repressor: The hCMV major immediate-early enhancer-promoter represents one of the most potent cis-regulatory units for directing the expression of transgenes in mammalian cells. In addition to the TATA element, a variety of upstream cis-acting element have been identified (FIG. 1) and, by interacting with cellular and viral transactivators, these elements ensure highly efficient transcription directed by the TATA element. Transcription initiation requires basal transcription factors to interact with the TATA element in a coordinate fashion to form a transcription pre-initiation complex. The TATA-binding protein (TBP) is the first and only basal transcription factor to interact with DNA specifically and the binding of TBP to the TATA element signals the transcription of the promoter. The present experiments were designed to test whether the tetracycline repressor can convert the hCMV major immediate-early enhancer-promoter into a regulatory switch by interacting with two tet operators about 10 base pairs downstream of the hCMV TATA element in plasmid pWRG1630. The tet operator sequences were positioned so that the tet repressor would bind to the same side of the DNA helix as the TATA-binding protein. Based upon their close proximity, it was hypothesized that the binding of the tet repressor to the tet operator would either block the binding of the TBP to the TATA element or interfere with the assembly of the pre-initiation complex directly.

Vero cells were transfected with 0.5 μg of pWRG1630 or pCMVtetOEGF either alone or in the presence of 1 μg, 2 μg, and 3 μg of the tet repressor expressing plasmid pcDNA3-tetR in medium either with no tetracycline or with tetracycline at a concentration of 1 μg per ml. Extracellular medium was collected from transfected cells every 20–24 hours, followed by the addition of fresh growth medium either with or without 1 μg of tetracycline. The hEGF concentration in the collected extracellular medium was determined by ELISA.

Figure 2B:
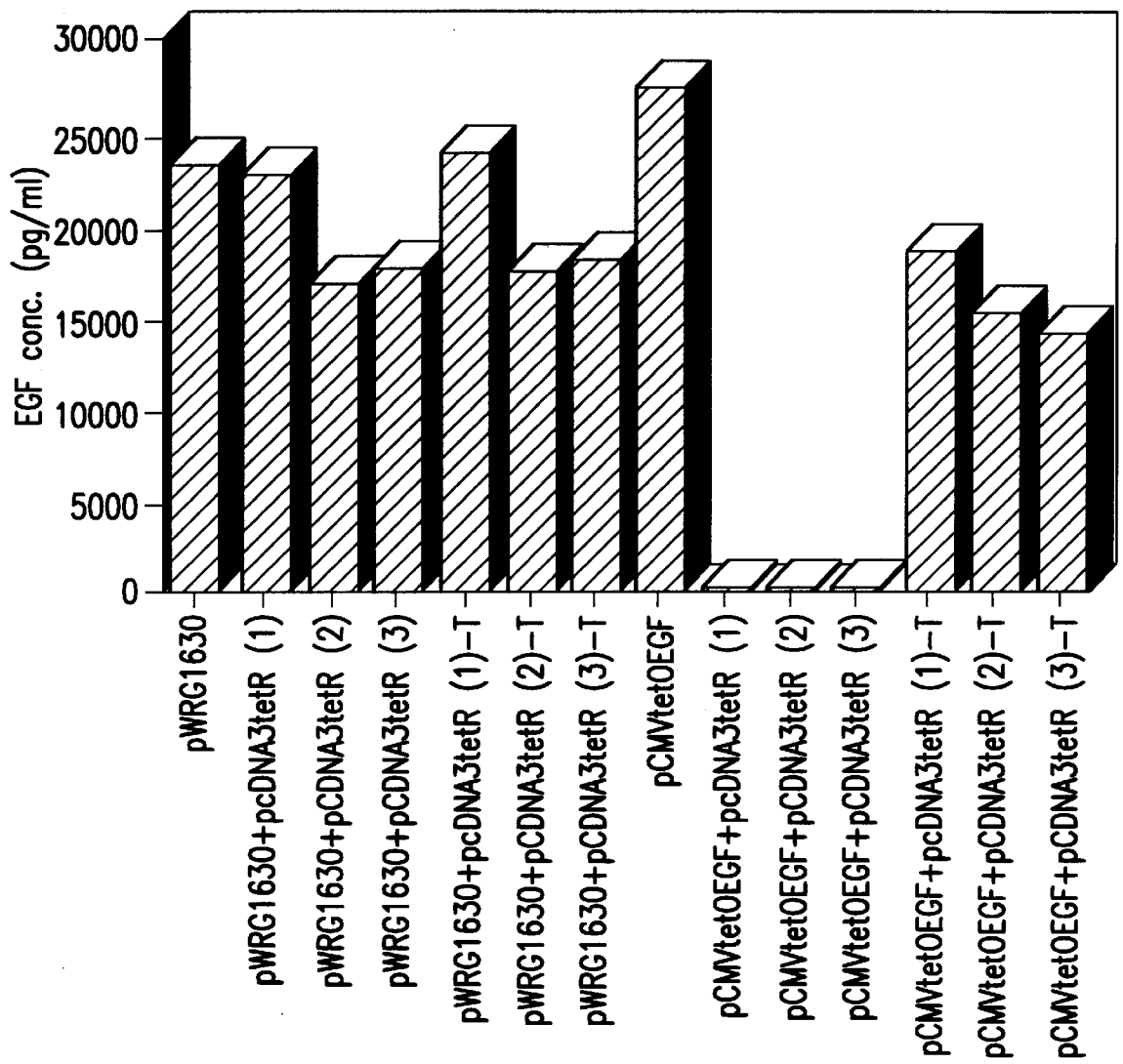
Figure 2C:
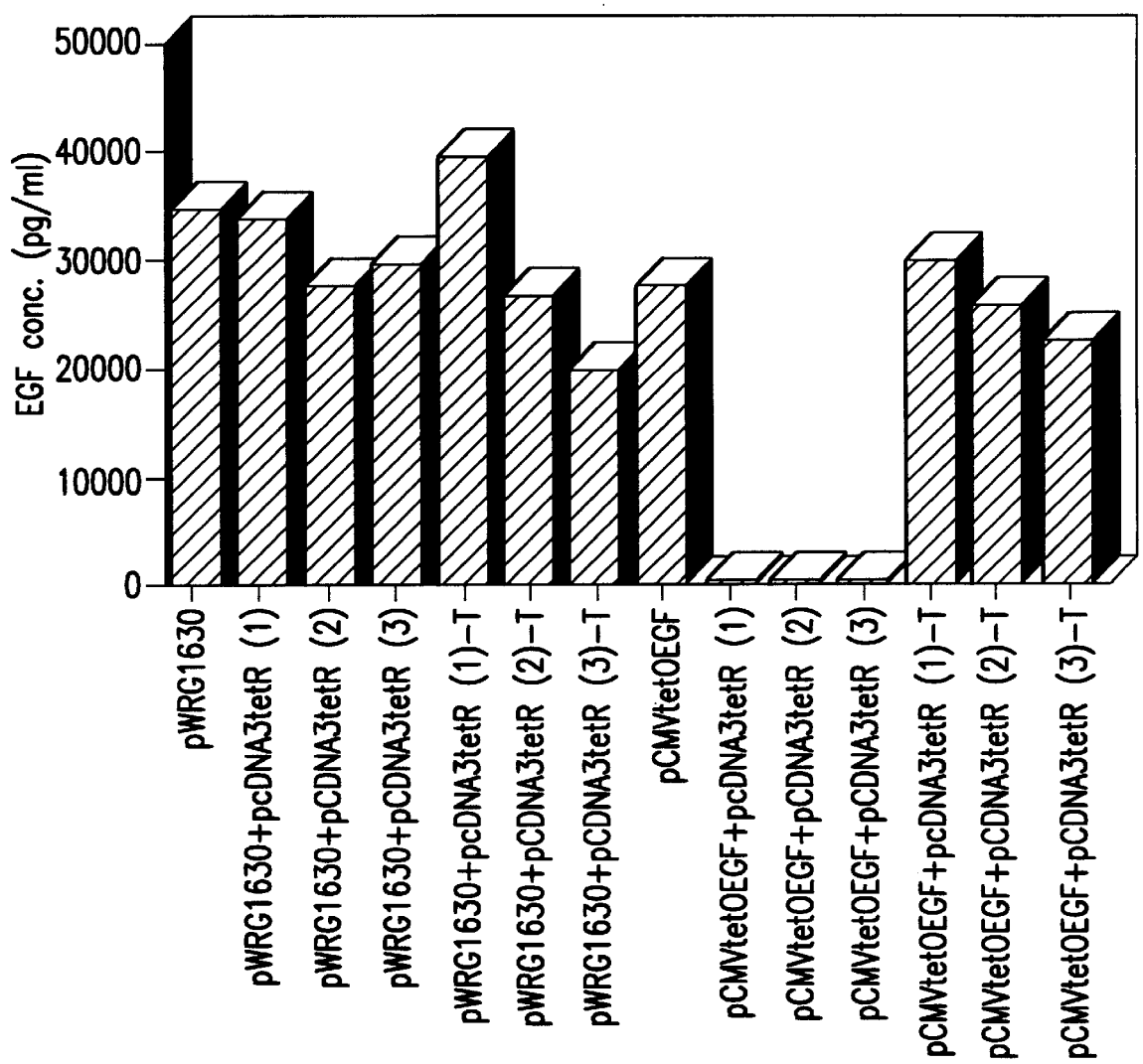

The results shown in FIG. 2 demonstrate that the expression of human EGF from pWRG1630 was not affected by the presence of pcDNA3-tetR and that the insertion of the tet-operator containing sequence near the hCMV major immediate-early enhancer-promoter has no effect on human EGF expression in the absence of tetR. Expression of EGF from pCMVtetOEGF was significantly reduced in the presence of tetR in a dose and time dependent manner. In the presence of 3 μg of tetR repressor-expressing plasmid, i.e,. pcDNA3-tetR, EGF expression from pCMVtetOEGF was repressed approximately 200 fold at 20 hours post-transfection, 1000 fold at 20–24 hours post-transfection, and 3500 at 44–68 hours post-transfection in the absence of tetracycline. Little or no repression was observed in the presence of tetracycline. In the presence of 2 μg of pcDNA3-tetR, approximately a 100-fold, 600-fold, and 2000-fold inhibition of expression was detected at 0–20 hours, 20–44 hours and 44–48 hours post-transfection. In the presence of 1 μg of pcDNA3-tetR, approximately a 60-fold, 100-fold, and 200-fold reduction in the synthesis of human EGF was observed at the three indicated time points. There was no human EGF expression in mock transfected Vero cells.

Figure 3A:
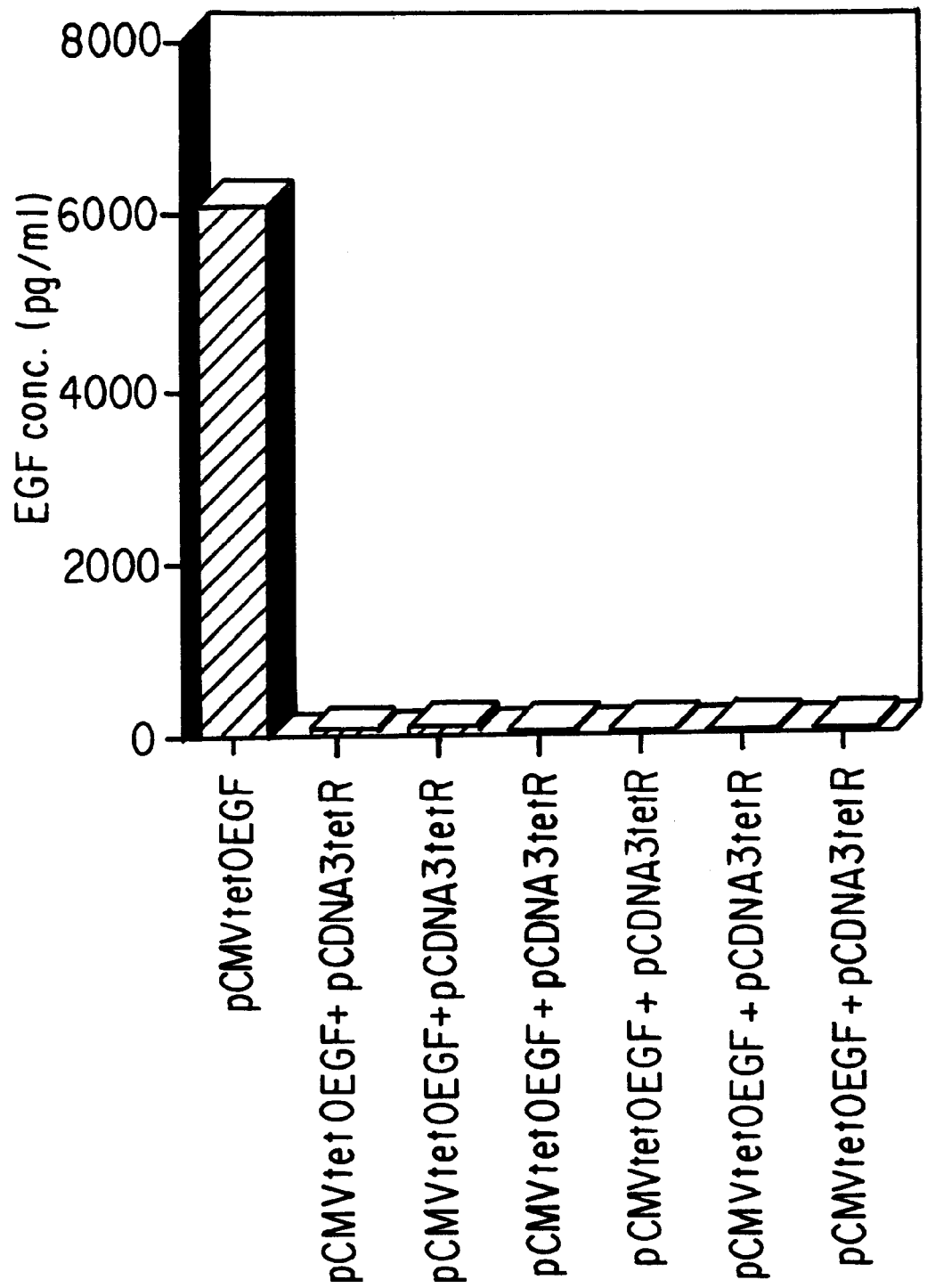
FIG. 3. Parts A–B Release of tetR-mediated repression by tetracycline. Vero cells were transfected with either pCM-VtetOEGF (0.5 $\mu$g) or pCMVtetOEGF (0.5 $\mu$g) and pcDNA3-tetR (2 $\mu$g) in the absence of tetracycline. 20 hours after transfection, extracellular medium was collected and fresh growth medium was added to the transfected cells in the absence or presence of tetracycline at 0.1 $\mu$g/ml or 1 $\mu$g/ml for an additional 24 hours. hEGF expression in extracellular medium collected from 0 to 20 hours (panel A) and 20 to 44 hours (panel B) was determined by ELISA. Two independent experiments are shown for each indicated co-transfection assay.
Figure 3B:
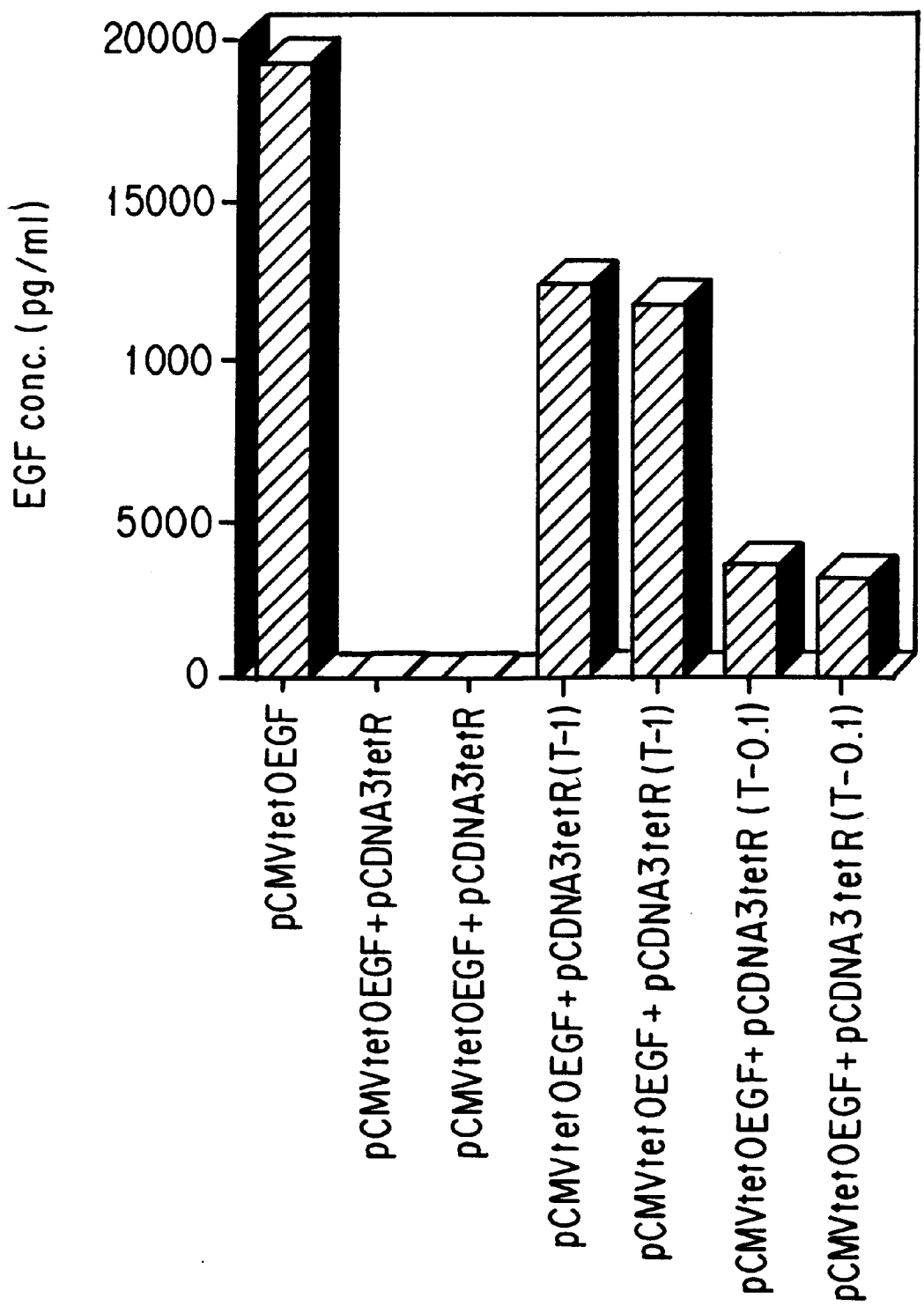

To test if tetR-mediated repression can be efficiently reversed by tetracycline, Vero cells were transfected with either pCMVtetOEGF alone or pCMVtetOEGF and pcDNA3-tetR in the absence of tetracycline from 0–20 hours (FIG. 3A) and in the presence or absence of tetracycline from 20–44 hours (FIG. 3B). The results demonstrate that the repression observed from 0–20 hours post-transfection can be efficiently reversed by the presence of 1 $\mu$g/ml of tetracycline while 0.1 $\mu$g/ml of tetracycline is not sufficient to reverse tetR-mediated repression under the conditions tested. Consistent with the experiments presented in FIG. 2, the data demonstrated that the basal promoter activity of pCMVtetOEGF was reduced 100–200 fold during 0–20 hours post-transfection, and about 500 fold from 20–44 hours post-transfection in the presence of 2 $\mu$g of pcDNA3-tetR.

Figure 4:
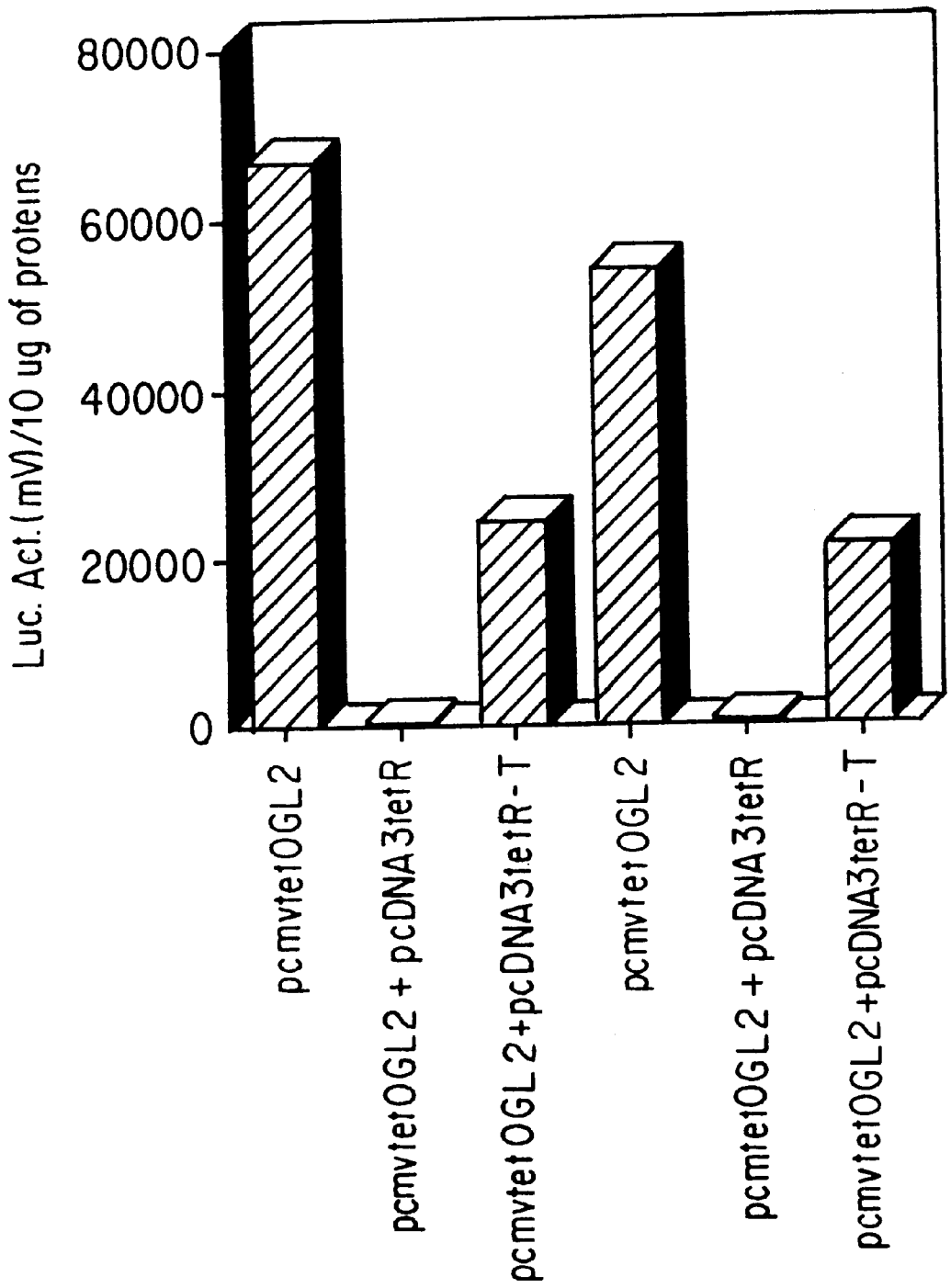
FIG. 4. Determination of the efficacy of tetR-mediated cumulative regulation of transgene expression using luciferase as a reporter. Vero cells in 60 mm dishes were transfected with 0.5 $\mu$g pCMVtetOGL2 alone or 0.5 $\mu$g of pCMVtetOGL2 together with 2 $\mu$g of pCDN3-tetR in the absence of tetracycline from 0 to 20 hours and in the absence or presence of 1 $\mu$g/ml of tetracycline from 20 to 70 hours. At 70 hours after transfection, Vero cells were lysed in 0.5 ml of 1 x luciferase lysis buffer in the presence of 0.2 mM of PMSF, 100 $\mu$g/ml of TPCK and 1 mM of leupeptin for 15 minutes at room temperature. Insoluble cellular debris was removed by centrifugation in a microcentrifuge for 20 minutes at 4° C. and luciferase activity was then measured as mV per 10 $\mu$g of protein.

Having demonstrated the kinetics of tetR-mediated regulation of the hCMV major immediate-early enhancer-promoter with a secretable peptide, human EGF, the ability of this system to regulate the expression of a non-secretable polypeptide, firefly luciferase was tested. FIG. 4 shows the results of two independent experiments in which Vero cells were either transfected with 0.5 $\mu$g of pCMVtetOGL2 alone, or co-transfected with 0.5 $\mu$g of pCMVtetOGL2 and 2 $\mu$g of pcDNA3-tetR in the presence or absence of 1 $\mu$g/ml of tetracycline. The levels of luciferase expression from pCMVtetOGL2 were decreased at least 100-fold in the presence of the tetR-expressing plasmid, pcDNA3-tetR, and it was found that this repression could be released efficiently by tetracycline. The level of luciferase expression from the wild-type hCMV immediate-early enhancer-promoter are not affected by the presence of pcDNA3-tetR. When similar experiments were performed on HeLa cells, a 40–50-fold repression was detected at 68–72 hours post-transfection. This indicates that, like the tetR-VP16 based activating system, the efficiency of the tetR-based repression is cell type dependent.

Figure 5:
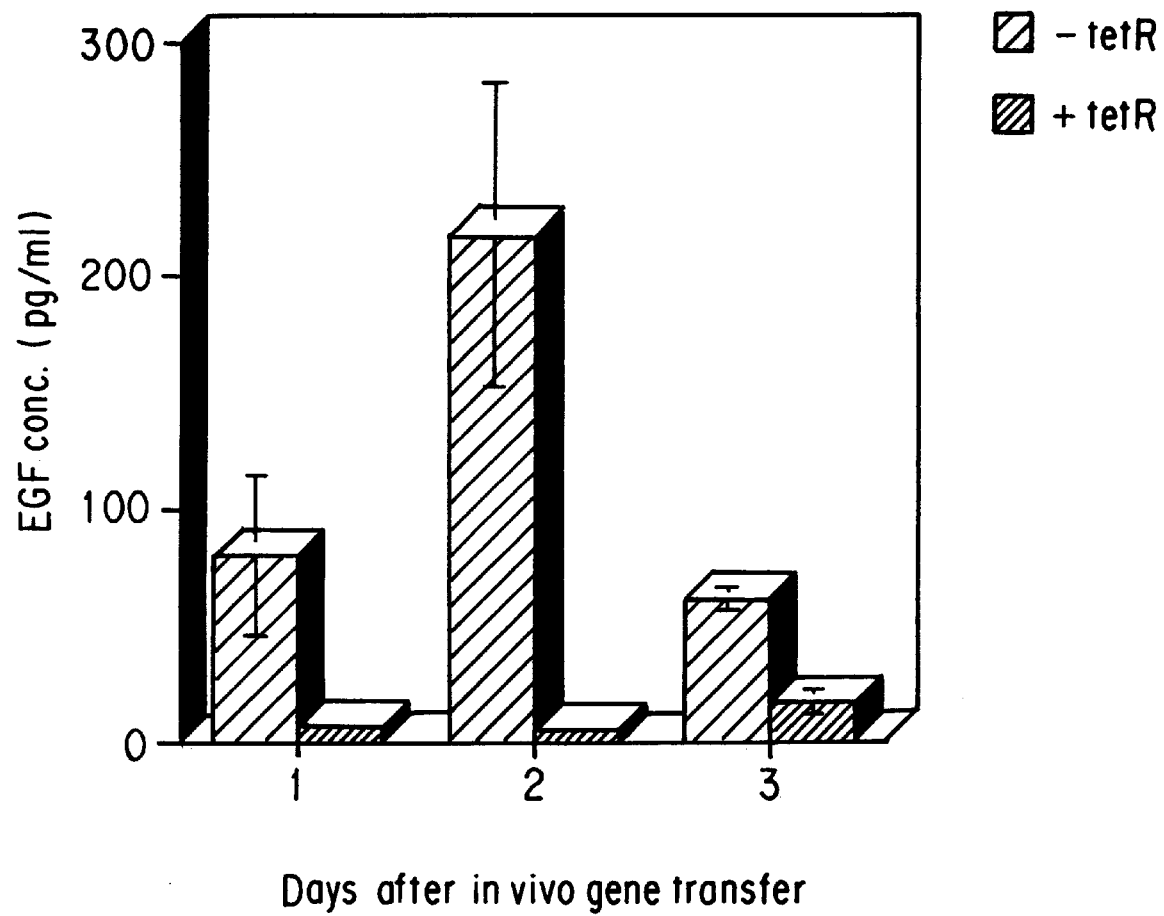
FIG. 5. In vivo regulation of the hCMV major immediate-early enhancer-promoter by the tet repressor. A total of 18 partial thickness wounds (15×15×15×1.2 mM) were created on porcine dorsal skin. Nine wounds received 0.2 $\mu$g of pCMVtetOEGF and 0.8 $\mu$g of pcDNA3 vector DNA and the others received 0.2 $\mu$g of pCMVtetOEGF and 0.8 $\mu$g of pcDNA3-tetR by particle-mediated gene transfer. After particle bombardment, each transfected wound was enclosed in a sealed vinyl adhesive chamber containing 1.2 ml of isotonic saline in the presence of 100 units/ml penicillin and 100 $\mu$g/ml streptomycin. Wound fluid was collected from the chambers at 22, 46 and 70 hours after gene transfer and stored at −70° C. Following collection of wound fluid at each indicated time point, a new chamber was applied. Each pig was given 500 mg of tetracycline by intravenous injection at 46 hours after gene transfer. hEGF expression in wound fluid was determined by ELISA. The vertical line associated with each bar represents standard error.
Figure 6:
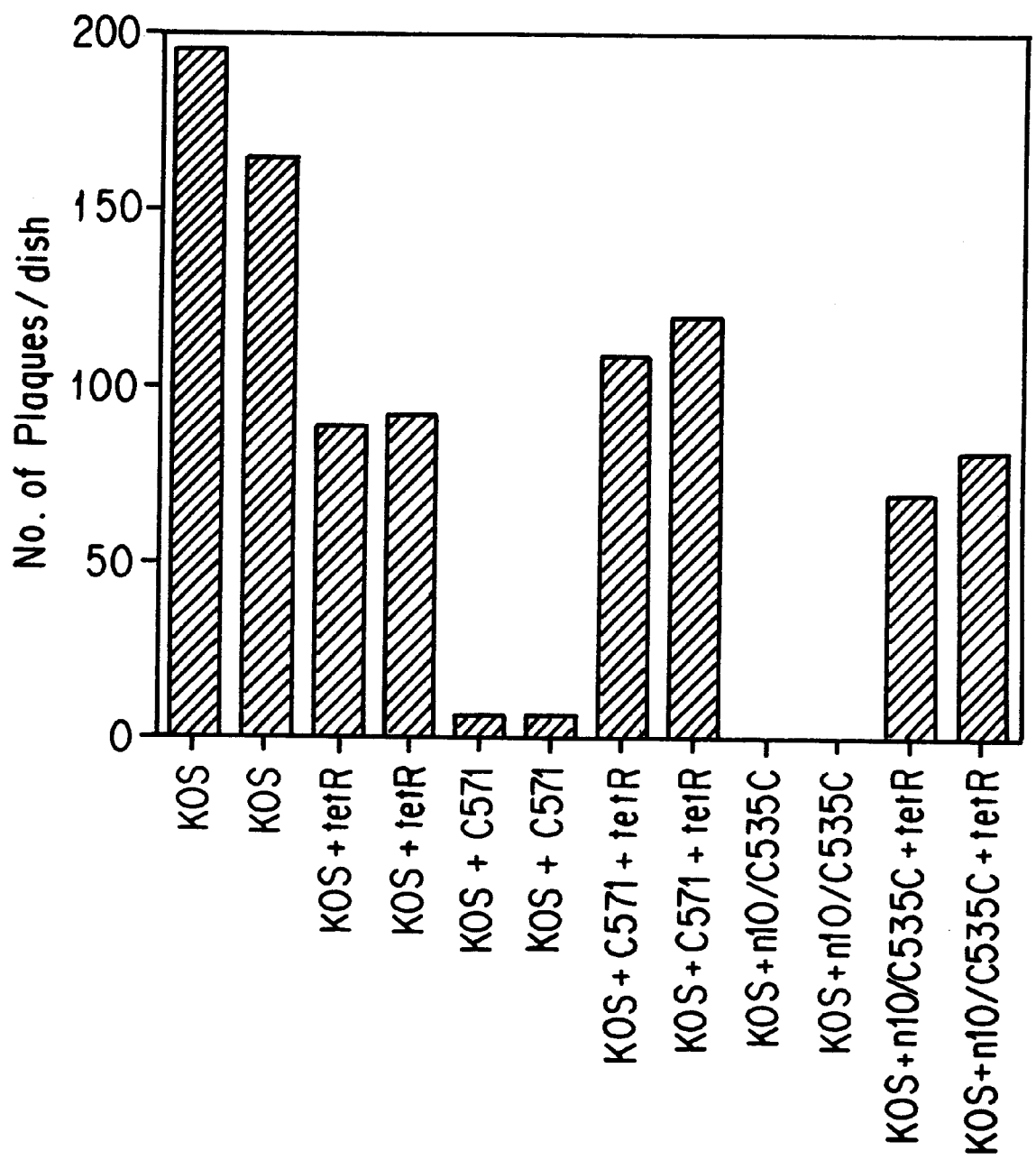
FIG. 6. Inhibition of HSV-1 replication by the transdominant negative form of the UL9 peptide and reversibility using the tet repressor. Vero cells were seeded at $5\times10^5$ cells per 60 mm. At 20 to 24 hours after seeding, the cells were transfected with 0.1 $\mu$g of purified infectious HSV-1 DNA either alone or in the presence of 0.1 $\mu$g of either pCMVtetOUL9-C571 or pCMVtetOUL9-n10/C535. Transfections were carried out in the presence of 1.5 $\mu$g of pCDNA3 vector DNA or the tet repressor-expressing plasmid, pCDNA3-tetR. Fourteen hours after transfection, medium was removed followed by the addition of methyl-cellulose to the transfected cells; at 10 ml per dish. Viral plaques were visualized by staining transfected cells with neutral red at 68 to 72 hours post-transfection and plates were counted 14 hours later.
Figure 7:
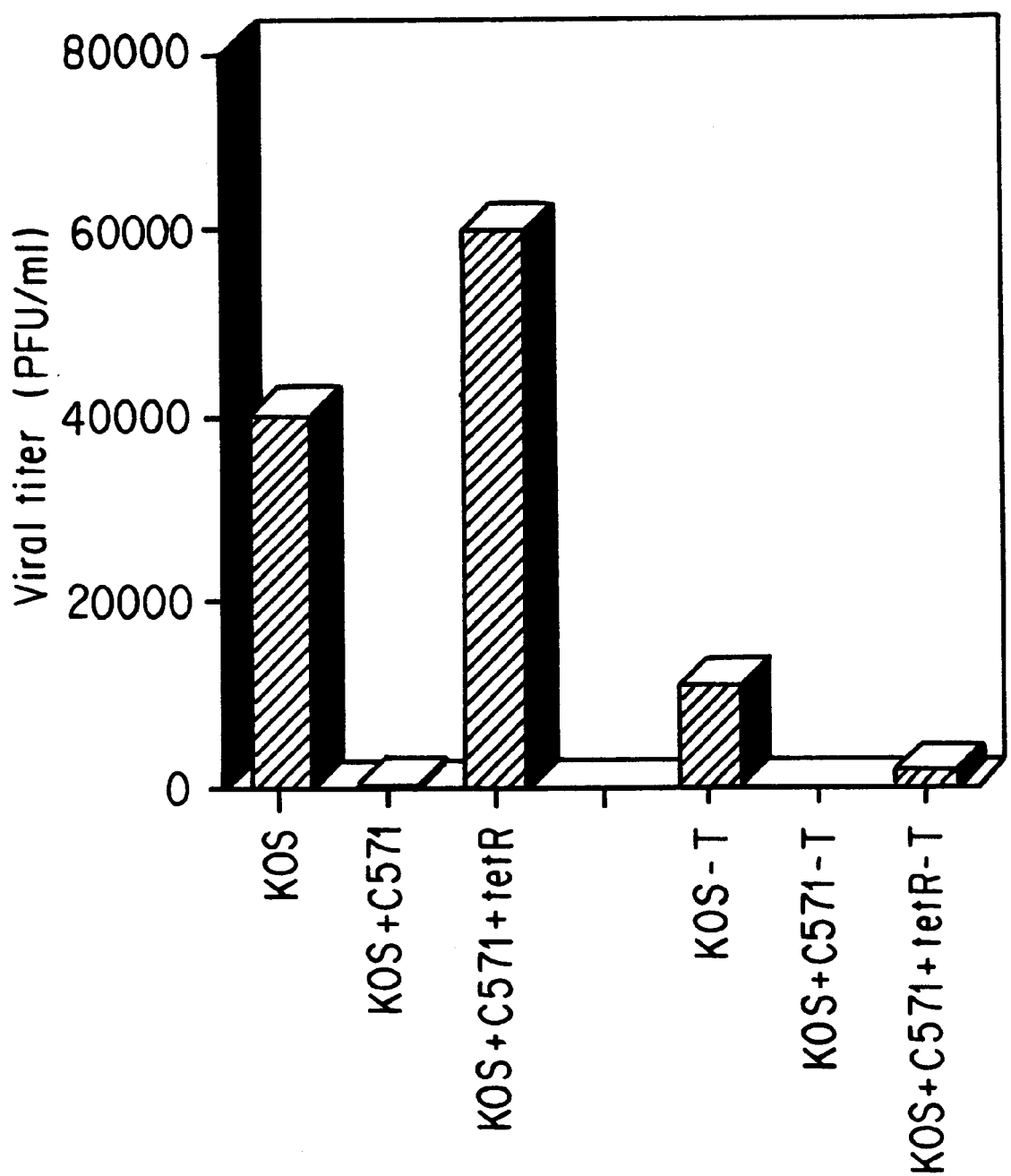
FIG. 7. Reversibility of HSV-1 replication inhibition using tetracycline. Vero cells were transfected with three different sets of DNA vectors: 1) 0.2 $\mu$g of infectious HSV-1 DNA and 2.1 $\mu$g of pCDNA3; 2) 0.2 $\mu$g of infectious HSV-1 DNA, 0.1 $\mu$g of pCMVtetOUL9-C571 and 2 $\mu$g of pCDNA3; and 3) 0.2 $\mu$g of infectious HSV-1 DNA, 0.1 $\mu$g of pCMVtetOUL9-C571 and 2 $\mu$g of pCDNA3-tetR. Transfections were carried out either in the presence or absence of tetracycline at 1 $\mu$g/ml. Sixteen hours after transfection, medium was removed from cells and 5 ml of fresh medium was added to each dish either with or without tetracycline at a concentration of 5 μg/ml. At 48 hours after transfection, cells were harvested and virus yields were determined. The results of this determination are shown in the figure.

In Vivo Regulation of the hCMV Major Immediate-Early Enhancer-Promoter by the Tetracycline Repressor: The data presented above demonstrate that: (1) the tet repressor is capable of acting as a potent sequence-specific trans-repressor in cultured mammalian cells; and (2) that the insertion of two tandem operators about 10 base pairs downstream of the promoters TATA element, converts the promoter into an effective tetracycline-dependent transcriptional switch. To test if this tetR-tet operator regulatory unit is functional in vivo, partial thickness wounds were created on porcine dorsal skin, with nine wounds receiving 0.2 $\mu$g of pCMVtetOEGF and 0.8 $\mu$g of pcDNA3 vector DNA and nine wounds receiving 0.2 $\mu$g of pCMVtetOEGF and 0.8 $\mu$g of pcDNA3-tetR per wound. As shown in FIG. 5, human EGF expression in partial thickness wounds co-transfected with pcDNA3-tetR was significantly lower than that observed in partial thickness wounds co-transfected with pcDNA3 vector plasmid in the absence of tetracycline. A 13-fold repression was detected one day after gene transfer.

Notably, although human EGF expression in pCMVtetOEGF transfected wounds was increased approximately 3-fold from day one to day two post-gene transfer, yields of human EGF in partial thickness wounds co-transfected with pcDNA3-tetR were reduced 1.5-fold. Collectively, in the presence of tetR, levels of human EGF expression were repressed approximately 55-fold at day two post-gene transfer in the absence of tetracycline. It is of particular significance that, upon receiving tetracycline through intravenous injection from day 2 to day 3 post-gene transfer, the tetR-mediated repression was released as evidenced by a 4-fold increase of human EGF expression in wounds receiving both pCMVtetOEGF and pcDNA3-tetR. In wounds transfected with pcMVtetOEGF alone, there was about a 4-fold reduction in EGF expression from day 2 to day 3 post-gene transfer. This observation proves the feasibility of using this regulatory switch in controlling the expression of transgenes in gene therapy.

C. Discussion

Regulation of transgene expression in target cells represents one of the most critical and challenging aspects of gene therapy. Using the hCMV major immediate-early enhancer-promoter as a prototype mammalian cell promoter, it has been demonstrated that, placing tetracycline operators 10 base pairs of the TATA element, enables the tetracycline repressor to function as a potent repressor of gene expression in mammalian cells.

Recently, by fusing the KRAB repressor domain of the human KOX1 zinc-finger protein with the tet repressor and inserting DNA sequences encoding seven tet operators 685 base pairs upstream of the transcription initiation site, it has been shown that the tet-KRAB chimeric protein, but not tetr alone, can suppress the hCMV major immediate-early enhancer-promoter approximately 10–15-fold in HeLa cells in a transient expression assay using luciferase as a reporter (Deuschle, et al., *Mol. Cell. Biol.* 15:1907–1914 (1995)). Using a different strategy, in which tet operators were inserted 10 base pairs, a full helix turn, downstream of the TATA element, it has been shown that the hCMV major immediate-early enhancer-promoter can be tightly regulated by tetR alone. Based on the study of Heuer & Hillen (*J. Mol. Biol.* 202:407–415 (1988)) it was hypothesized that this specific design would place the tet repressor on the same side of the DNA helix as TBP and the binding of tetR to the tet operator provides a direct steric block for TBP. Using hEGF as a secretable promoter, the kinetics of tetR-mediated repression was explored. Close to a 4000-fold repression was observed in vitro at 3 days post-transfection. Combining a porcine wound model with particle-mediated gene transfer, this study has provided a direct in vivo confirmation of this tetR-mediated regulatory switch in fine tuning the expression of transgenes for gene therapy.

Unlike other tet repressor/operator regulatory systems, e.g., the tetR-VP16 based activating and tetR-KRAB repressor system, the regulatory switch disclosed herein does not require the use of tetracycline repressor/mammalian cell transactivator or repressor fusion proteins to achieve its effects. Thus, the potential pleiotropic effects on the expression of cellular genes caused by cellular transcription factors are minimal and higher levels of expression of the regulator (i.e., the tetracycline repressor) can be achieved. Notably, the efficacy of the tetR-mediated regulatory switch was found to vary significantly in vitro as compared to in vivo. This apparent difference can probably be explained by: 1) differences in the means of gene transfer which may lead to different co-transfection efficiency; and 2) differences in cell types.

Example 2

Viral Replication Switch

To test whether the tetR-regulated transcription switch discussed above can be converted into a novel viral replication switch to regulate de novo viral production in a reversible fashion and produce a transdestructive recombinant virus, the following experiments were performed using herpes simplex virus type 1 as a prototype.

A. Construction of Trans-dominant Negative HSV-1 UL9 Mutant Polypeptide Expressing Plasmids The UL9 protein is one of the seven HSV-1 essential gene products that are directly involved in viral replication. UL9 binds specifically to the HSV-1 origin of DNA replication. It is a nuclear phosphoprotein 851 amino acids in length. Studies have shown that the C-terminal amino acids 535–851 of UL9 contain the DNA binding domain of the protein and, when over-expressed, it can block virus DNA replication in a dominant negative fashion.

In order to clone, the C-terminal 317 amino acids of UL9 and place it under the control of the tet operator-containing hCMV major immediate-early enhancer-promotor, the Bam HI-Not I EGF-containing fragment in plasmid pCMVte-tOEGF was replaced by the Bam HI-EcoR V UL9-containing fragment from plasmid pSP6UL9. The resulting plasmid was designated pCMVtetOUL9-C571 and expresses the C-terminal amino acids 571–851 of UL9.

To construct plasmid pCMVtetOUL9-n10/C535, a plasmid expressing a UL9 protein fragment containing amino acids 1 to 10 of UL9 and amino acids 535 to 851 of UL9, a double stranded oligo encoding the first 10 amino acids of the UL9 protein followed by amino acids Thr-Met-Gly was inserted into the Bam HI site of pCMVtetOUL9-C571. Plasmid pCMVtetOUL9-C535C, which expresses the C-terminal amino acids 535 to 851 of UL9, was constructed by the religation of Bam HI-Kpn I digested pCMVtetOUL9-n10/C535.

B. Transient Inhibition Analysis of HSV-1 Replication

To test if the mutant UL9 polypeptides encoded by pCMVtetOUL9-C571 and pCMVtetOUL9-n10/C535 can function as trans-dominant negative mutant polypeptides inhibiting HSV-1 replication, and, most importantly, to test whether an inhibitory effect can be regulated by the tet repressor, Vero cells were seeded at $5 \times 10^5$ cells per 60 nm. At 20 to 24 hours after seeding, the cells were transfected with 0.1 micrograms of purified infectious HSV-1 DNA alone or co-transfected with 0.1 micrograms of pCMVtetOUL9-C571 or pCMVtetOUL9-n10/C535 in the presence of 1.5 micrograms of pcDNA3 vector DNA or the tet repressor-expressing plasmid, pcDNA3-tetR, by lipofectin. At 14 hours post transfection, the lipofectin-DNA containing transfection medium was removed followed by addition of methylcellulose to the transfected cells at 10 ml per dish. Viral plaques were visualized by staining transfected dishes with neutral red at 68 to 72 hours post transfection and counting 14 hours later. As shown in FIG. 1, co-transfection of infectious HSV-1 DNA with pCMVtetOUL9-C571 reduces the viral placque forming efficiency approximately 30 fold. When co-transfected with pCMVtetOUL9-n10/C535C, the placque forming efficiency of infectious HSV-1 DNA was reduced at least 100 fold. Significantly, both C571- and n10/C535C-mediated repression of HSV-1 DNA replication can be efficiently silenced by the tet repressor. When a similar experiment was performed with pCMVtetOUL9-C535C, the placque formation of HSV-1 DNA was reduced at least 200 fold and again, this C535C-mediated repression can be efficiently reversed by tetR.

Having demonstrated that the inhibitory effects of the trans-dominant negative C-terminal UL9 polypeptides on HSV-1 replication can be efficiently silenced by the tet repressor, the specificity of this tetR related viral replication switch was further investigated. Vero cells were transfected with: 1) 0.2 micrograms of infectious HSV-1 DNA and 2.1 micrograms of pcDNA3; 2) 0.2 micrograms of infectious HSV-1 DNA, 0.1 micrograms of pCMVtetOUL9-571 and 2 micrograms of pcDNA3; and 3) 0.2 micrograms of infectious HSV-1 DNA, 0.1 micrograms of pCMVtetOUL9-C571 and 2 micrograms of pcDNA3-tetR. Transfections were carried out either in the absence or the presence of tetracycline at 1 microgram per ml. At 16 hours post transfection, the transfection medium was removed and 5 ml of fresh medium was added to each dish with either no tetracycline or tetracycline at a concentration of 5 micrograms per ml. At 48 hours post transfection, cells were harvested and virus yields were determined. The data presented in FIG. 2 demonstrate that: 1) C571-mediated expression of HSV-1 replication can be reversed by the tet repressor; and 2) this tetR-regulated reversion of HSV-1 replication is tetracycline specific as evidenced by the effect of pCMVtetOUL9-571 on HSV-1 placque forming units was significantly reduced in the presence of tetracycline.

Collectively, these observations demonstrate that, by combining transdominant negative mutant viral polypeptides with the tetR-regulated potent mammalian transcription switch, a novel viral replication switch can be generated. In principle, any polypeptide or antisense RNA that is capable of inhibiting viral productive infection can be incorporated into this novel viral replication switch. Using this switch, a trans-destructive or inhibitory viral vector can be generated while tetR is not present in the viral genome. This trans-inhibitory viral vector is not only capable of serving as a vehicle for in vivo gene transfer, but is also capable of inhibiting the endogenous and/or latent virus replication. This invention can also be used for generating a viral vaccine which not only is capable of inducing an effective host immune response, but which is also able to function as a therapeutic agent helping to eliminate endogenous viral infection when encountered within the same cell.

All references cited herein are fully incorporated by reference. Having now fully described the invention, it will be understood by those of skill in the art that the invention may be practiced and wide and equivalent range of conditions, parameters and the like, without affecting the spirit or scope of the invention or any embodiments thereof.

What is claimed is:

1. A recombinant DNA molecule comprising:
   a) a mammalian promoter sequence having a TATA element;
   b) at least one tet operator sequence positioned at least 6 nucleotides 3' to the TATA element; and
   c) a gene lying 3' to said operator and operably linked to said promoter.

2. The recombinant DNA of claim 1, wherein said tetracycline operator sequence is positioned between 6 and 24 nucleotides 3' to said TATA element.

3. The DNA molecule of claim 1, wherein said promoter is the human cytomegalovirus (hCMV) immediate-early promoter.

4. The DNA molecule of claim 1, further comprising a gene encoding the tet repressor protein.

5. A host cell transformed with a vector comprising the DNA molecule of claim 1.

6. A method for producing recombinant protein in a mammalian cell that makes the tet repressor protein, said method comprising:

a) transforming said mammalian cell with a vector comprising:
      i) a mammalian promoter sequence having a TATA element;
      ii) at least one tet operator sequence positioned at least 6 nucleotides 3' to the TATA element; and
      iii) a gene lying 3' to said tet operator and operably linked to said promoter wherein said gene encodes said recombinant protein;
   b) introducing tetracycline into the transformed cells of step a) to induce the expression of said gene and produce said recombinant protein.

7. The method of claim 6, wherein said tet operator sequence is positioned between 6 and 24 nucleotides 3' to said TATA element.

8. The method of claim 6, wherein said promoter is the human CMV immediate-early promoter.

* * * * *

UNITED STATES PATENT AND TRADEMARK OFFICE
CERTIFICATE OF CORRECTION

PATENT NO : 5,972,650
DATED : October 26, 1999
INVENTOR(S): Feng Yao

It is certified that error appears in the above-identified patent and that said Letters Patent is hereby corrected as shown below:

In column 1, line 4, of the patent, after the title and before the section entitled "Field of the Invention," please add:

-- Statement of Government Support
The work leading to this invention was supported by one or more grants from the U.S. Government. The U.S. Government therefore has certain rights in the invention. --

Signed and Sealed this

Seventh Day of March, 2000

Attest:

Q. TODD DICKINSON

*Attesting Officer*

*Commissioner of Patents and Trademarks*

UNITED STATES PATENT AND TRADEMARK OFFICE
CERTIFICATE OF CORRECTION

| | | |
|---|---|---|
| PATENT NO. | : 5,972,650 | Page 1 of 1 |
| APPLICATION NO. | : 08/883327 | |
| DATED | : October 26, 1999 | |
| INVENTOR(S) | : Feng Yao | |

It is certified that error appears in the above-identified patent and that said Letters Patent is hereby corrected as shown below:

In column 1, after the title and before the heading "Field of the Invention" that appears on line 5, a paragraph should be added citing Government funding. The added paragraph should read as follows:

-- Statement of Government Support
This invention was made with Government support under Grant No. GM051449 awarded by the National Institutes of Health. The U.S. Government therefore has certain rights in the invention. --

Signed and Sealed this

Eighteenth Day of August, 2009

David J. Kappos
*Director of the United States Patent and Trademark Office*